US009834221B2

(12) United States Patent
Nilsson

(10) Patent No.: US 9,834,221 B2
(45) Date of Patent: Dec. 5, 2017

(54) DRIVER ATTENTIVENESS DETECTION METHOD AND DEVICE

(71) Applicant: Benny Nilsson, Alingsas (SE)

(72) Inventor: Benny Nilsson, Alingsas (SE)

(73) Assignee: AUTOLIV DEVELOPMENT AB, Vargarda (SE)

( * ) Notice: Subject to any disclaimer, the term of this patent is extended or adjusted under 35 U.S.C. 154(b) by 88 days.

(21) Appl. No.: 14/436,658

(22) PCT Filed: Oct. 19, 2012

(86) PCT No.: PCT/SE2012/051133
§ 371 (c)(1),
(2) Date: Apr. 17, 2015

(87) PCT Pub. No.: WO2014/062107
PCT Pub. Date: Apr. 24, 2014

(65) Prior Publication Data
US 2015/0258997 A1  Sep. 17, 2015

(51) Int. Cl.
*B60W 40/09* (2012.01)
*A61B 5/18* (2006.01)
(Continued)

(52) U.S. Cl.
CPC ............ *B60W 40/09* (2013.01); *A61B 3/113* (2013.01); *A61B 5/18* (2013.01); *B60K 28/06* (2013.01);
(Continued)

(58) Field of Classification Search
CPC .......... B60W 40/09; B60W 2040/0827; B60K 28/02; G06K 9/00604; G06K 9/00845; G08B 21/06
(Continued)

(56) References Cited

U.S. PATENT DOCUMENTS 6,154,559 A    11/2000  Beardsley
2006/0164218 A1*  7/2006  Kuttenberger ........ G01S 13/931
340/435
(Continued)

FOREIGN PATENT DOCUMENTS

EP    2 143 585 A1    3/2011
EP    2 426 001 A1    3/2011
(Continued)

OTHER PUBLICATIONS

PCT International Search Report—dated Jul. 19, 2013.

*Primary Examiner* — Omar Casillashernandez
(74) *Attorney, Agent, or Firm* — Brinks Gilson & Lione

(57) ABSTRACT

A driver attentiveness detection device and method using at least one digital camera device (2) and a control unit (5). The camera device (2) is arranged to detect eye configurations of a vehicle driver (4). The control unit (5) compares the detected eye configurations with previously stored models of eye configuration samples (13, 14, 15, 16) which are indicative of eyes that look inside or outside a predetermined field of view (6). The control unit (5) further determines whether the detected eye configurations are looking inside or outside the predetermined field of view from the comparison, and is also arranged to indicate when the vehicle driver (4) has been determined to be looking outside the predetermined field of view (6) to a predetermined extent.

20 Claims, 6 Drawing Sheets

(51) Int. Cl.
  *B60K 28/06*   (2006.01)
  *A61B 3/113*   (2006.01)
  *G08B 21/06*   (2006.01)
  *G06K 9/00*    (2006.01)
  *A61B 3/11*    (2006.01)

(52) U.S. Cl.
  CPC ..... *G06K 9/00604* (2013.01); *G06K 9/00845* (2013.01); *G08B 21/06* (2013.01)

(58) Field of Classification Search
  USPC .......................................................... 340/576
  See application file for complete search history.

(56) References Cited

U.S. PATENT DOCUMENTS

| | | | | |
|---|---|---|---|---|
| 2006/0202843 | A1* | 9/2006 | Ota | G06K 9/2036 340/576 |
| 2008/0049185 | A1* | 2/2008 | Huffman | A61B 3/113 351/206 |
| 2008/0185207 | A1 | 8/2008 | Kondoh | |
| 2010/0033333 | A1* | 2/2010 | Victor | A61B 3/113 340/576 |
| 2012/0002843 | A1* | 1/2012 | Yoda | A61B 5/1103 382/103 |
| 2012/0133528 | A1* | 5/2012 | Lee | B60K 28/066 340/945 |
| 2012/0212353 | A1* | 8/2012 | Fung | B60K 28/06 340/905 |
| 2012/0242819 | A1 | 9/2012 | Schamp | |
| 2013/0050258 | A1* | 2/2013 | Liu | G06F 3/005 345/633 |

FOREIGN PATENT DOCUMENTS

| | | |
|---|---|---|
| EP | 2 298 155 A3 | 4/2014 |
| WO | WO 2012087245 A2 * | 6/2012 ......... G06K 9/00255 |

* cited by examiner

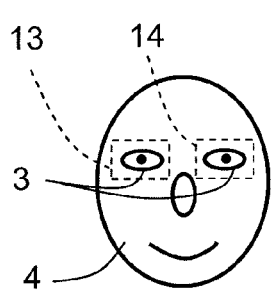
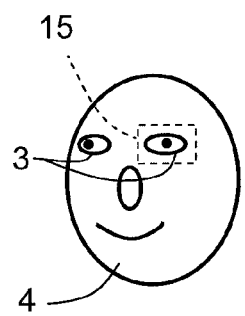
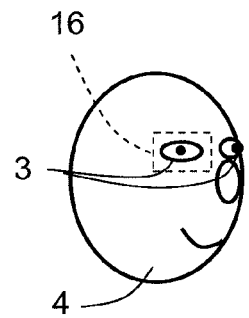
FIG. 5a    FIG. 5b    FIG. 5c
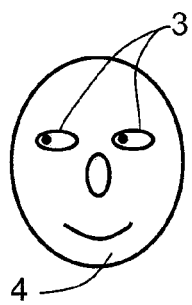
FIG. 6a    FIG. 6b    FIG. 6c

DRIVER ATTENTIVENESS DETECTION METHOD AND DEVICE

CROSS REFERENCE TO RELATED APPLICATIONS

This application claims priority to PCT International Patent Application No. PCT/SE2012/051133, filed on Oct. 19, 2012.

FIELD OF THE INVENTION

The present invention relates to a method for detecting decreased attentiveness of a vehicle driver, the method including the step of detecting eye configurations of the vehicle driver.

The present invention also relates to a vehicle driver attentiveness detection device having at least one digital camera device and a control unit, said camera device being arranged to detect eye configurations of a vehicle driver.

BACKGROUND

Detection of vehicle driver attentiveness is desirable since loss of, or in any way deteriorated, attentiveness impairs the ability of a vehicle to control the vehicle and to be aware of the surroundings. Examples of vehicles are motor vehicles, trains, aircraft and boats. It may also be desirable to detect attentiveness for operators of industrial equipment and the like.

A problem regarding deteriorated attentiveness is that, generally, persons do not detect their own lack of attentiveness when it appears. It is thus difficult for a person to be aware of lack of attentiveness, and to take action for counteraction. Deteriorated attentiveness may be due to different factors such as distracting objects or gadgets as well as drowsiness.

Today, many devices and methods for detecting attentiveness of a vehicle driver are known, and in most cases one or more digital cameras capture images of a vehicle driver's head features and the position of the eyes in order to calculate a gaze angle, and to determine whether the gaze falls within a gaze window. If the calculated gaze angle indicates that the gaze falls outside the gaze window for one or several predetermined amounts of time, it is determined that the driver is inattentive, which result in an alarm and/or other security actions.

Present attentiveness detection systems may use algorithms using advanced generic gaze and headtracking software. Such software creates models of the face which are used to calculate the head and gaze directions. For these models to work, they must track several points on the eyes, nose and mouth. If some of these points are covered or tracked incorrectly, the performance degrades rapidly, leaving present systems fairly unstable. An example of such a system is disclosed in EP 2298155.

There is thus a need for a device and a method for detecting vehicle driver attentiveness which is less complex and more robust than previously known equipment of this kind, and where the risk of false alerts or other types of malfunctions is reduced.

INTRODUCTORY DESCRIPTION OF THE INVENTION

The above object is achieved by means of a method for detecting decreased attentiveness of a vehicle driver, the method including the step of detecting eye configurations of the vehicle driver.

The method further includes the steps:

Analyzing the detected eye configurations by comparing the detected eye configurations with previously stored models of eye configuration samples. The stored models of eye configuration samples are indicative of eyes that look inside and/or outside a predetermined field of view.

Determining whether the detected eye configurations are looking inside the predetermined field of view or outside the predetermined field of view using said analysis.

Indicating when the vehicle driver has been determined to be looking outside the predetermined field of view to a predetermined extent.

The object is also achieved by means of a vehicle driver attentiveness detection device having at least one digital camera device and a control unit, said camera device being arranged to detect eye configurations of a vehicle driver. The control unit is arranged to compare the detected eye configurations with previously stored models of eye configuration samples. The stored models of eye configuration samples are indicative of eyes that look inside or outside a predetermined field of view. The control unit is further arranged to determine whether the detected eye configurations are looking inside the predetermined field of view or outside the predetermined field of view. The control unit is furthermore arranged to indicate when the vehicle driver has been determined to be looking outside the predetermined field of view to a predetermined extent.

According to an example, the indication of when the vehicle driver has been determined to be looking outside the predetermined field of view to a predetermined extent includes the production of an output signal which is indicative of vehicle driver inattentiveness.

According to another example, the output signal is used for triggering an alarm and/or one or more vehicle safety systems.

According to another example, the predetermined field of view is in the form of a volume that extends in a vehicle forward running direction.

As an example, the volume may extend to an imaginary end surface, positioned at a certain distance from the driver, where the detected eye configurations are determined to be looking inside the predetermined field of view if they are determined to be looking at the imaginary end surface.

According to another example, so-called Haar features may be used for modeling eye configuration samples.

Other examples are disclosed in this description.

A number of advantages are obtained by means of the present invention. Mainly, a much less complicated device and method for detection of vehicle driver attentiveness by determining where a driver is looking is provided, without the need for calculating such things as gaze angles, head angles and models for facial features.

BRIEF DESCRIPTION OF THE DRAWINGS

The present invention will now be described more in detail with reference to the appended drawings, where:

FIG. 5a shows a schematic first example of a driver with a positive eye configuration sample;

FIG. 5b shows a schematic second example of a driver with a positive eye configuration sample;

FIG. 5c shows a schematic third example of a driver with a positive eye configuration sample;

FIG. 6a shows a schematic first example of a driver with a negative eye configuration sample;

FIG. 6b shows a schematic second example of a driver with a negative eye configuration sample;

FIG. 6c shows a schematic third example of a driver with a negative eye configuration sample;

DETAILED DESCRIPTION

Figure 1:
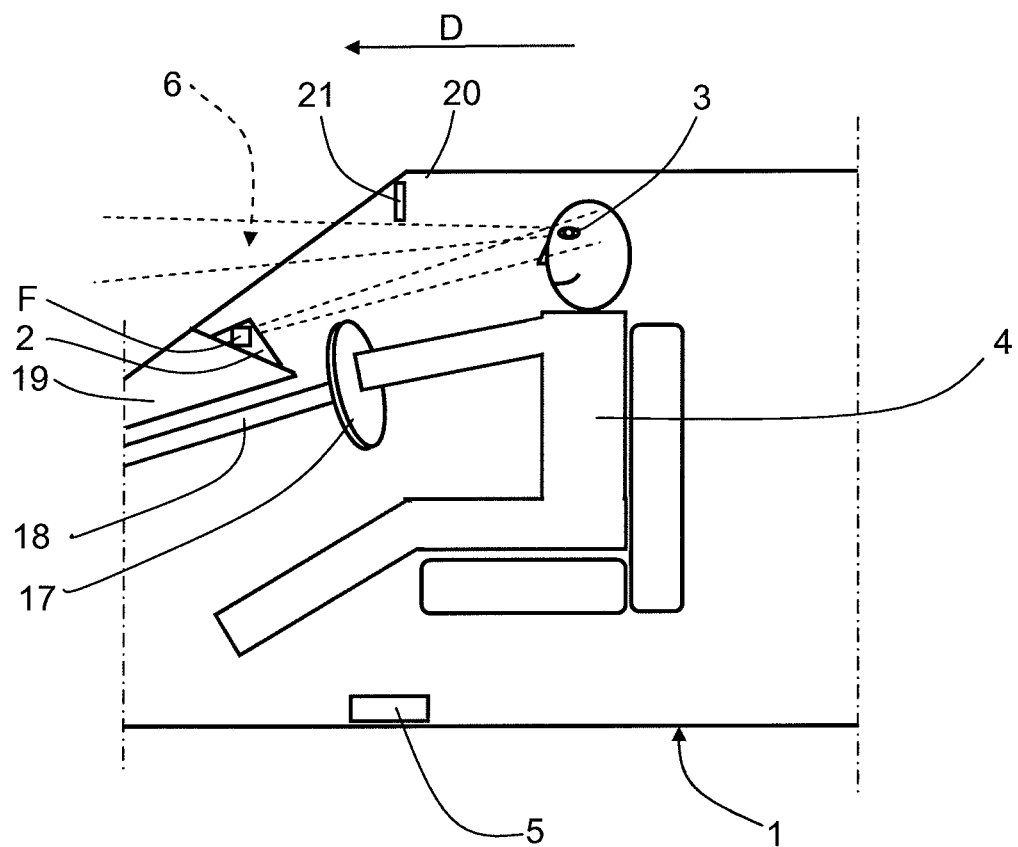
FIG. 1 shows a schematic partial cut-open side view of a vehicle with a driver.

FIG. 1 schematically shows a cut-open part of a vehicle 1 arranged to run on a road 12 in a direction D, where the vehicle 1 includes a near infrared (NIR) digital camera device 2 positioned on the dashboard with two NIR light sources F such as flashes (only one NIR light source is shown in FIG. 1, the other NIR light source is assumed to be positioned on the other side of the camera device). The digital camera device 2 is arranged for capturing images of the eyes 3 of a person 4 driving the vehicle 1, a driver, and transferring these images to a control unit 5. These images are used for determining whether the driver 4 is looking at the road ahead or not, which in turn is a measure of the driver's attentiveness.

With reference to FIGS. 1, 2, 3, and 4, a volume 6 is defined in front of the driver 4, where the volume 6 is limited by four imaginary border walls 7, 8, 9, 10 that run from the driver 4 towards a rectangular imaginary end surface 11 which is positioned a certain distance L from the driver 4 in the forward running direction D. The rectangular imaginary end surface 11 is most clearly indicated in FIG. 4 as a dashed rectangle at an end of the imaginary border walls 7, 8, 9, 10. The imaginary end surface 11 may thus be regarded to either define the imaginary border walls 7, 8, 9, 10, or to be defined by the imaginary border walls 7, 8, 9, 10.

Figure 2:
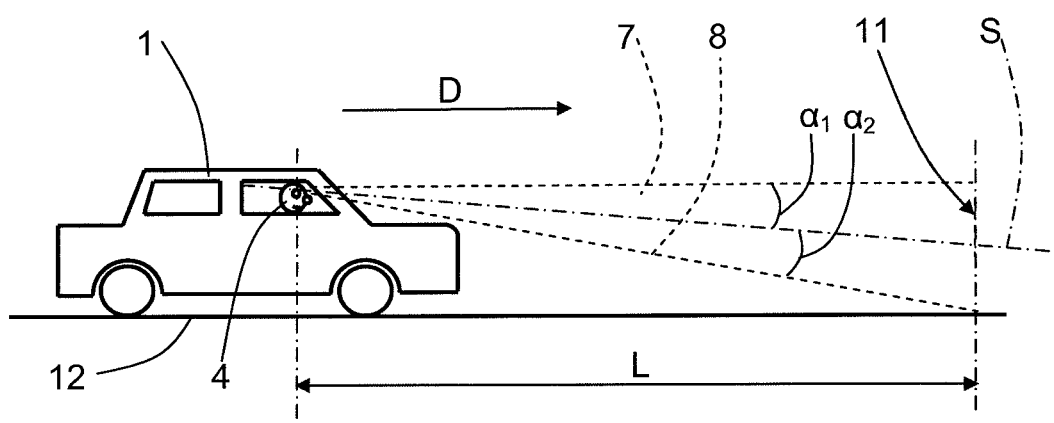
FIG. 2 shows a schematic side view of the vehicle with the driver and a predetermined volume corresponding to a predetermined field of view.
Figure 3:
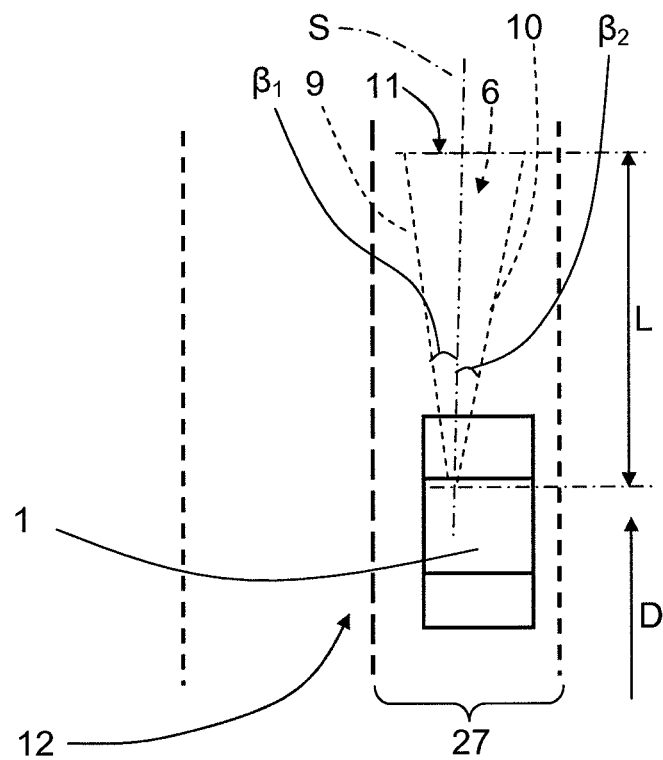
FIG. 3 shows a schematic top view of the vehicle and the predetermined volume.
Figure 4:
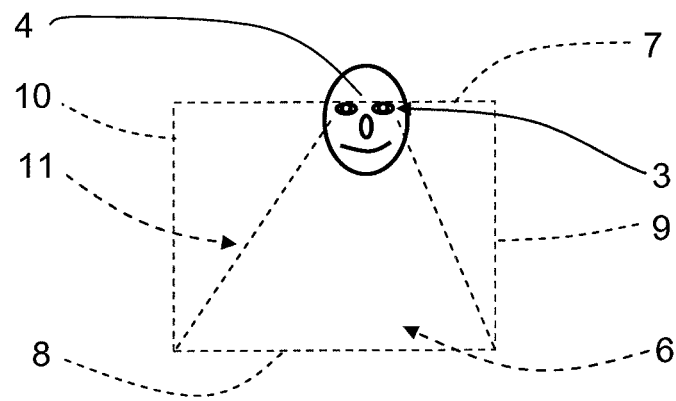
FIG. 4 shows a schematic front view of the driver and the predetermined volume.

As shown in FIG. 2, FIG. 3 and FIG. 4, the imaginary border walls 7, 8, 9, 10 divert from each other from the driver 4 towards the imaginary end surface 11 such that a first imaginary border wall 7 and a second imaginary border wall 8 face each other and the road 12 with a first elevation inclination $\alpha_1$ and a second elevation inclination $\alpha_2$, and a third imaginary border wall 9 and a fourth imaginary border wall 10 face each other with a first azimuth inclination $\beta_1$ and a second azimuth inclination $\beta_2$, and run perpendicular to the road 12. Preferably, the first imaginary border wall 7 runs horizontally in a level that coincides with a standard driver's eyes, and the second imaginary border wall 8 is inclined such that its part of the imaginary end surface 11 approximately is in level with the road 14. This is not necessary, but should be regarded as an example of the volume's extension.

The inclinations $\alpha_1, \alpha_2; \beta_1, \beta_2$ are measured with respect to a reference line S, where the elevation inclinations $\alpha_1, \alpha_2$ constitute elevation zone angles $\alpha_1, \alpha_2$ at each side of the reference line S, the elevation zone angles for example being of the magnitude 15°-20°. The azimuth inclinations $\beta_1, \beta_2$ constitute azimuth zone angles $\beta_1, \beta_2$ at each side of the reference line S, the azimuth zone angles for example being of the magnitude 10°-20°. It is also conceivable that the zone angles in a plane are of unequal values.

The reference line S is in this example defined as a line that runs through the volume 6 such that the elevation zone angles $\alpha_1, \alpha_2$ are mutually equal and such that the azimuth zone angles $\beta_1, \beta_2$ are mutually equal.

As shown in FIG. 3, and also as indicated in FIG. 4, keeping the azimuth zone angles $\beta_1, \beta_2$ equal, the reference line S and thus the volume 6 is slightly inclined to the right in an azimuth plane with reference to the forward running direction D. This is due to the fact that in this example, the driver 4 is sitting on the left-hand side of the road 12 and is driving on a right-hand sided lane 27 of the road 12. Keeping the eyes 3 on the lane 27 in question means that the driver 4 has to look slightly to the right with reference to the forward running direction D.

While it is determined that the driver 4 is looking inside the volume 6, i.e. looking at some part of the imaginary end surface 11, the driver 4 is considered to be attentive to the road ahead. On the other hand, when it is determined that the driver 4 is looking outside the volume 6, i.e. not looking at some part of the imaginary end surface 11, the driver 4 is considered to be inattentive to the road ahead.

According to the present invention, the control unit 5 is arranged to determine whether the driver 4 is looking inside the volume 6 by analyzing detected images of the eyes 3, these images being indicative of certain eye configurations. The analysis is performed by comparing the detected eye configurations with previously stored models of eye configuration samples 13, 14, 15, 16. The stored models of eye configuration samples 13, 14, 15, 16 are indicative of eyes that look inside a predetermined field of view, in this example the volume 6 defined above. How these models of eye configuration samples are created will be discussed later in the description. The comparison is carried out by means of a suitable video processing algorithm such as the well-known Viola-Jones method using so-called Haar features, such algorithms are well-known in the field of image processing, and details of these will not be discussed further.

If the analysis results in that the detected eye configurations are determined to be looking outside the predetermined field of view 6 to a predetermined extent, the control unit is arranged to produce an output signal that is indicative of vehicle driver inattentiveness. The predetermined extent may for example be a certain time and also exceeding a predetermined buffer as will be discussed in a later part of the description.

The predetermined extent may also relate to whether one or two eyes in the detected eye configurations are determined to be looking inside or outside the predetermined field of view 6. A detected eye configuration may thus be determined to be looking inside the predetermined field of view 6 if one eye in the detected eye configuration is looking in the predetermined field of view 6. This means that the stored models of eye configuration samples 13, 14, 15, 16 are indicative of eyes that look inside the predetermined field of view 6 if such a model sample only is indicative of one eye that is looking in the predetermined field of view 6.

Such an output signal may result in a number of alternative actions. According to one example, an alert system may be activated, such that an acoustic or optical signal is triggered. Furthermore, triggering of vibrating means in the chair or a steering wheel 17 is also conceivable, as well as activation of a motorized seatbelt retractor.

Preferably, a buffer routine is used to delay the determining that the driver is inattentive. For example, an eyes-offthe-road warning should not be triggered until around 3-5 seconds of eyes-off-the-road time has been buffered.

Before the buffer becomes active, there is an initialization phase where the control unit 5 is arranged to determine the passing of a predetermined time of continuous detected eye configurations that are looking inside the predetermined field of view, an example of such a predetermined time is 1-2 seconds, constituting an initialization buffer threshold. This is to verify that there is a driver 4 present, and that the system is working properly; for example when a driver 4 takes place in the vehicle 1, or after a false alarm. If the time of continuous detected eye configurations that are looking inside the predetermined field of view is interrupted before the predetermined time is reached, the initialization phase is re-started. An initialization buffer may be used for keeping track of detected eye configurations in the initialization phase.

After a successful initialization phase, the normal buffer is active, and the eye configurations of the driver 4 are now detected for evaluating a possible decreased attentiveness of the driver 4 as disclosed above, in an online phase.

The control unit 5 is preferably arranged to force a re-initialization if the buffer time increases past a predetermined time interval constituting a buffer threshold, for example 5-10 seconds, without the control unit 5 having determined that the vehicle driver is inattentive, thus without the control unit 5 issuing said signal. This is also with the intent to decrease the risk of false alarms. In this case, the control unit is arranged to re-start the initialization phase.

Figure 7:
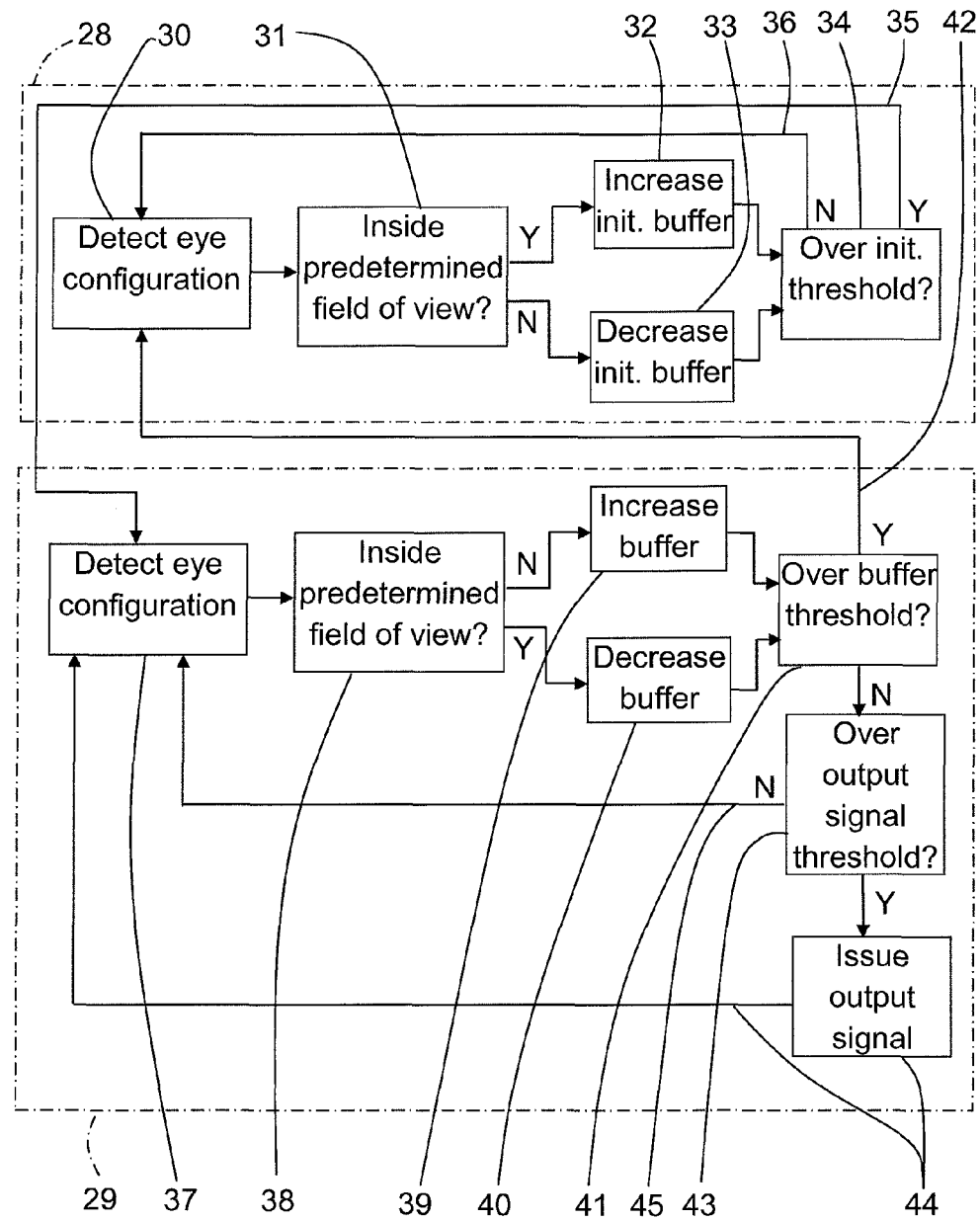
FIG. 7 shows a flowchart for an example of an initialization phase and an online phase.

The above is indicated in FIG. 7, where the initialization phase 28 and the online phase 29 mentioned above are disclosed in a flowchart.

In the initialization phase 28, the following steps are performed:
30: Detect eye configurations.
31: Are detect eye configurations within the predetermined field of view 6?
32: If "Yes", increase initialization buffer.
33: If "No", decrease initialization buffer.
34: Has the initialization buffer threshold been passed?
35: If "Yes", then go to the online phase.
36: If "No", then go back to the start 30 of the initialization phase 28.

In the online phase 29, the following steps are performed:
37: Detect eye configurations.
38: Are detect eye configurations within the predetermined field of view 6?
39: If "Yes", decrease buffer.
40: If "No", increase buffer.
41: Has the buffer threshold been passed?
42: If "Yes", then go back to the start 30 of the initialization phase 28.
43: If "No", has the threshold for issuing an output signal indicative of vehicle driver inattentiveness been passed?
44: If "Yes", issue an output signal indicative of vehicle driver inattentiveness, then go back to the start 36 of the online phase 29.
45: If "No", then go back to the start 30 of the online phase 29.

To avoid false alarms, the control unit 5 is further preferably arranged to retain the output signal that is indicative of vehicle driver inattentiveness during and a certain time after certain conditions, such as during turns when the steering wheel angle exceeds a predetermined value, such as for example 10°-15°, when the turn indicator is activated and when turns are detected by means of GPS (Global Positioning System), camera devices and/or inertia sensors.

Alternatively, in a curve, the volume may be adapted to follow a driver's natural gaze when entering and running in the curve.

In the above, the output signal has been described to activate an alert system, but as stated previously, such an output signal may result in a number of alternative actions. Alternatively, or additionally, peripheral security systems may be enhanced, triggered or activated, such as automatic braking systems. In this context, it should be noted that alert systems normally are best suited for high speed driving, on for example highways, while many other security systems such as automatic braking systems are adapted to work at low speed driving, for example in cities.

To trigger an early automatic braking, when applicable, an appropriate buffer time might be a few hundred milliseconds; enough to not activate on blinks but to activate relatively quickly when the driver looks away from the road.

In many applications it's also preferred to decrease the buffer at a faster rate and to empty it after a predefined eyes-on-the-road time. All of the settings described above need to be specifically set depending on what kind of system that the buffer is connected to.

The present invention is normally arranged either for high speed driving or low speed driving, but may also be arranged to work at both. An example of this will be discussed later.

When the present invention is arranged for high speed driving, the output signal may be retained at speeds falling below a predetermined value, such as for example 60 kph (kilometers per hour). In this way, false alarms at low speed driving, for example in cities, are avoided. This is due to the fact that in cities, the driver's eyes 3 are normally looking at the road close to the vehicle, and the head is usually moving in order to keep track of, for example, other vehicles, pedestrians, traffic lights and different signs. Such behavior would not be permitted at high speed driving.

The distance L to the imaginary end surface 11 is for example 10 meters, but this is only an example of a suitable length. By positioning the imaginary end surface 11 at such a distance away from the driver 4, parallax errors and sensitivity for different heights of drivers are lowered. A length of about 10 meters is also best suited for the case when the present invention is arranged for high speed driving.

As an example, since the driver's eyes 3 normally are looking at the road close to the vehicle in cities, the distance L could be altered to be of a lesser magnitude when low speed driving is detected, for example at speeds falling below a predetermined value, such as the previously mentioned 60 kph. In this way, the present invention may be arranged to run in both a high speed driving mode and a low speed driving mode by altering the distance L in a suitable way with appropriate changes to the size of the imaginary end surface 11.

The control unit 5 is programmed with mathematical models of positive eye configuration samples and negative eye configuration samples. Examples of positive eye configuration samples 13, 14, 15, 16 are constituted by the images inside the dashed boxes in FIG. 5a-FIG. 5c. Examples of negative eye configuration samples can be found in FIG. 6a-FIG. 6c, where in this case the whole images are used for defining the negative eye configuration samples. The eye configuration samples are collected in any suitable way, and are converted to mathematical models, for example by means of the Viola-Jones method using said Haar features.

The process of acquiring mathematical models of positive eye configuration samples and negative eye configuration samples is sometimes referred to as "training". As an example of how the mathematical models of positive eye configuration samples and negative eye configuration samples are acquired, how the so-called "training" may be performed, the following method may be used.

First, the collected images are analyzed by means of an eye tracking arrangement which is adapted to detect gaze angels. Eye tracking arrangements of different types are previously well-known. Then, positive eye configuration samples are selected, either automatically or manually. Finally, a suitable method such as the previously mentioned Viola-Jones method is used for finding suitable features.

The previously discussed elevation zone angles $\alpha_1$, $\alpha_2$ and azimuth zone angles $\beta_1$, $\beta_2$ are used during the "training", and there is preferably a play of 3-5 degrees. In this way, a grey zone which is ignored in in-car use is created.

For a robust and generalized functionality, it is very important to get a diverse selection of eye configuration samples from different conditions and different types of facial features.

By means of the present invention, the problems inherent with the prior art are bypassed by classifying the driver's state of attentiveness by detecting the eyes 3 only, without calculating any gaze or head angles. By using image object detection algorithms, a classifier in the control unit 5 is trained to detect eyes only looking in a predetermined direction, such as within the volume 6 discussed above.

Figure 8:
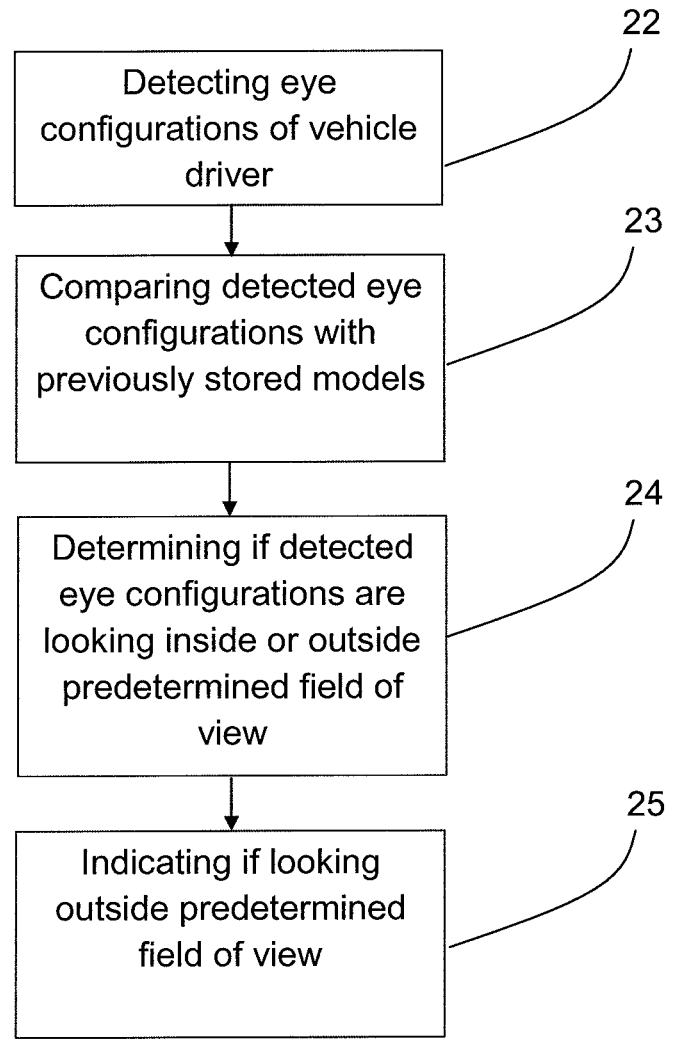
FIG. 8 shows a flowchart for a general method according to the present invention.

With reference to FIG. 8, the present invention relates to a general method for detecting the level of alertness of a vehicle driver, the method comprising the steps:
22: Detecting eye configurations of the vehicle driver 4.
23: Analyzing the detected eye configurations by comparing the detected eye configurations with previously stored models of eye configuration samples 13, 14, 15, 16. The stored models of eye configuration samples 13, 14, 15, 16 are indicative of eyes that look inside and/or outside a predetermined field of view 6.
24: Determining whether the detected eye configurations are looking inside the predetermined field of view 6 or outside the predetermined field of view 6 using said analysis.
25: Indicating when the vehicle driver 4 has been determined to be looking outside the predetermined field of view 6 to a predetermined extent.

The present invention is not limited to the examples above. For example, there may be one or more NIR cameras 2 and one or more NIR flashes F, where the control unit 5 is arranged to send trigger signals to the camera 2 and flashes F. The camera 2 should be placed as close as possible to the line of sight of the driver 4 when the driver 4 is looking forward. However, the placement is more important in the horizontal direction than the vertical direction. Other types of camera systems, with or without flashes, are conceivable. One advantage with an infrared camera is that it does not matter if the driver's eyes are obscured, for example by sunglasses.

Examples for camera positions are at the steering wheel 17 rim or spokes, at the steering column 18, at the dashboard 19 or in the inner roof lining 20 as indicated in FIG. 1. Other examples are airbag covers, sun visor, an inner rear-view mirror assembly 21, and in the vehicle A-pillars.

If the camera 2 is positioned straight in front of the driver 4, it is less complicated to determine if the driver 4 is looking inside the predetermined field of view due to more available data. However, for practical reasons this may not be possible due to space limitations, design reasons and view obstructive reasons.

The control unit 5 might be formed by one or several units, and may also be integrated in another unit such as a vehicle restraint control unit.

The predetermined field of view and the imaginary end surface 11 may have any suitable form, for example the imaginary end surface may be oval or polygonal. The volume may thus be defined by more walls than the four walls discussed in the example above. It is also conceivable that there is only one wall that is suited for a round or oval imaginary end surface.

In the above, it is determined whether the driver 4 looks in the predetermined field of view by using stored models of eye configuration samples that are indicative of eyes that look inside a predetermined field of view. It is possible that stored models of eye configuration samples that are indicative of eyes that look outside a predetermined field of view, or both, are used instead.

The comparison is carried out by means of a suitable video processing algorithm, such algorithms are well-known and details of these will not be discussed further. A typical video processing algorithm may use stored models of eye configuration samples that are indicative of eyes that look inside a predetermined field of view and stored models of head and eye configuration samples that are indicative of eyes that look outside a predetermined field of view as indicated above, where it is stated that the whole images shown in FIG. 6a-FIG. 6c are used for defining negative eye configuration samples. This is of course only an example of which stored models that are needed and how they are used. Generally, stored models of eye configuration samples that are indicative of eyes that look inside or outside a predetermined field of view are used.

Generally, the control unit 5 is arranged to indicate that the vehicle driver 4 has been determined to be looking outside the predetermined field of view 6 to a predetermined extent. Such an indication may comprise producing an output signal which is indicative of vehicle driver inattentiveness.

While the above description constitutes the preferred embodiment of the present invention, it will be appreciated that the invention is susceptible to modification, variation and change without departing from the proper scope and fair meaning of the accompanying claims.

The invention claimed is:

1. A method for detecting decreased attentiveness of a vehicle driver, the method comprising the steps of:
   detecting eye configurations of the vehicle driver;
   analyzing the detected eye configurations by comparing the detected eye configurations with previously stored models of eye configuration samples, the stored models of eye configuration samples being indicative of eyes that look inside or outside a predetermined field of view;
   determining whether the detected eye configurations are looking inside the predetermined field of view or outside the predetermined field of view using the analysis;
   indicating when the vehicle driver has been determined to be looking outside the predetermined field of view to a predetermined extent, wherein the field of view extends to an imaginary end surface, positioned at a predetermined distance (L) from the driver, the predetermined distance having a greater value at high vehicle speeds than at low vehicle speeds; and
   upon indicating that the driver is looking outside the predetermined field of view to the predetermined extent, generating an output signal activating at least one of a driver alert system or an automatic brake system, wherein the predetermined extent includes a buffer time of the vehicle driver looking outside the predetermined field of view reaching a buffer threshold, wherein the buffer time is initiated when it is determined that the vehicle driver has been continuously looking inside the predetermined field of view for an initialization buffer time equaling an initialization buffer threshold, and wherein the step of generating the output signal is suspended while the vehicle is traveling at a speed below 60 km/h.

2. The method according to claim 1, wherein the step of indicating when the vehicle driver has been determined to be looking outside the predetermined field of view to a predetermined extent comprises producing an output signal which is indicative of vehicle driver inattentiveness.

3. The method according to claim 2, wherein the output signal is configured for triggering an alarm or one or more vehicle safety systems.

4. The method according to claim 1, wherein the predetermined field of view is a volume that extends in a vehicle forward running direction (D).

5. The method according to claim 4, wherein the volume extends to the imaginary end surface, positioned at a certain distance (L) from the driver, where the detected eye configurations are determined to be looking inside the predetermined field of view if they are determined to be looking at the imaginary end surface.

6. The method according to claim 1, wherein the stored models of eye configuration samples are modeled by using Haar features.

7. The method for detecting decreased attentiveness of a vehicle driver according to claim 1, wherein the stored models of eye configuration samples being indicative of eyes that look either inside or outside the predetermined field of view.

8. The method for detecting decreased attentiveness of a vehicle driver according to claim 1, further comprising providing a camera device for use in the detecting of eye configurations of the vehicle driver.

9. The method according to claim 3, wherein the output signal is used for triggering an alarm in the form of at least one of an acoustic signal, an optical signal, and a vibration.

10. A driver attentiveness detection device comprising at least one digital camera device and a control unit, the camera device being arranged to detect eye configurations of a vehicle driver, the control unit is configured to compare the detected eye configurations with stored models of eye configuration samples, wherein the stored models of eye configuration samples are indicative of eyes that look inside or outside a predetermined field of view, the control unit further being configured to determine whether the detected eye configurations are looking inside the predetermined field of view or outside the predetermined field of view, wherein the field of view extends to an imaginary end surface, positioned at a predetermined distance (L) from the driver, the predetermined distance having a greater value at high vehicle speeds than at low vehicle speeds, wherein the control unit furthermore is configured to indicate by generating an output signal when the vehicle driver has been determined to be looking outside the predetermined field of view to a predetermined extent, wherein the predetermined extent includes a buffer time of the vehicle driver looking outside the predetermined field of view reaching a buffer threshold, wherein the control unit is configured to initiate the buffer time when it is determined that the vehicle driver has been continuously looking inside the predetermined field of view for an initialization buffer time equaling an initialization buffer threshold, and wherein the device is configured to suspend the generation of the output signal while the vehicle is traveling at a speed below 60 km/h.

11. The device according to claim 10, wherein an indication by the control unit that the vehicle driver has been determined to be looking outside the predetermined field of view to a predetermined extent comprises the production of an output signal which is indicative of vehicle driver inattentiveness.

12. The device according to claim 11, wherein the output signal is arranged to trigger at least one of an alarm and one or more vehicle safety systems.

13. The device according to claim 10, wherein the predetermined field of view is a volume that extends in a vehicle forward running direction (D).

14. The device according to claim 13, wherein the volume extends to the imaginary end surface, positioned at a certain distance (L) from the driver, wherein the control unit is arranged to determine that detected eye configurations are looking inside the predetermined field of view if the control unit determines the driver is looking at the imaginary end surface.

15. The device according to a claim 10, wherein the camera device is of a near infrared type.

16. The device according to claim 10, wherein the camera device comprises a near infrared flash.

17. The device according to claim 10, wherein the camera device is positioned at one of a steering wheel rim or spokes, at a steering column, at a dashboard, in an inner roof lining, at an airbag cover, at a sun visor, at an inner rear-view mirror assembly, and in a vehicle A-pillar.

18. The device according to claim 10, wherein the stored models of eye configuration samples are indicative of eyes that look inside the predetermined field of view.

19. The device according to claim 12, wherein the output signal is the alarm in the form of at least one of an acoustic signal, an optical signal, and a vibration.

20. The device according to claim 10, wherein the control unit is configured to interrupt the output signal in the event that the vehicle is undergoing a maneuver including at least one of, a turn indicated by one of a steering wheel angle exceed a predetermined value, a turn signal is activated, a turn as indicated by a GPS signal, a turn as indicated by a camera device, and a turn as indicated by an inertia sensor.

* * * * *